(12) United States Patent
Bischoff et al.

(10) Patent No.: US 8,872,664 B2
(45) Date of Patent: Oct. 28, 2014

(54) MONITORING ACTIVITY OF AN INDIVIDUAL

(75) Inventors: Brian J. Bischoff, Red Wing, MN (US); Alan P. Shilepsky, Minneapolis, MN (US); Lina Long, St. Paul, MN (US)

(73) Assignee: Healthsense, Inc., Mendota Heights, MN (US)

( * ) Notice: Subject to any disclaimer, the term of this patent is extended or adjusted under 35 U.S.C. 154(b) by 18 days.

(21) Appl. No.: 13/324,711

(22) Filed: Dec. 13, 2011

(65) Prior Publication Data

US 2012/0086573 A1    Apr. 12, 2012

Related U.S. Application Data

(63) Continuation of application No. 11/788,178, filed on Apr. 19, 2007, now Pat. No. 8,164,461, which is a continuation-in-part of application No. 11/323,077, filed on Dec. 30, 2005, now Pat. No. 7,589,637.

(51) Int. Cl.
*G08B 23/00* (2006.01)
*G08B 21/04* (2006.01)
*G08B 25/01* (2006.01)
*G06F 19/00* (2011.01)
*G08B 21/02* (2006.01)

(52) U.S. Cl.
CPC ........ *G08B 21/0423* (2013.01); *G08B 21/0453* (2013.01); *G08B 25/016* (2013.01); *G06F 19/3418* (2013.01); *G08B 21/0492* (2013.01); *G08B 21/0288* (2013.01)
USPC .................. 340/573.1; 340/573.4; 340/573.7; 340/539.11; 340/521; 482/8; 482/9; 434/258

(58) Field of Classification Search
USPC .................. 340/573.1, 573.4, 573.7, 539.11, 340/539.12, 539.22, 521, 522; 482/8–9; 434/258–261
See application file for complete search history.

(56) References Cited

U.S. PATENT DOCUMENTS 5,400,246 A    3/1995   Wilson et al.
5,447,166 A    9/1995   Gevins (Continued)

FOREIGN PATENT DOCUMENTS

DE    1 952 2 803    1/1997
EP       1571583     9/2005

(Continued)

OTHER PUBLICATIONS

AIST, "Housing That Protects the Home-Make—Development of Technology Capable of Detecting Abnormalities in the Ordinary Living Pattern Home-Maker for Information Signaling and Health Management—", http://www/aist.go.jp/aist_e/latest_research/2003/20030221/20030221.html, AIST, 7 pgs., Feb. 3, 2003.

(Continued)

*Primary Examiner* — Hoi Lau
(74) *Attorney, Agent, or Firm* — Brooks, Cameron & Huebsch, PLLC

(57) ABSTRACT

Embodiments of the present invention relate to methods, devices, and systems to monitor activity. One method to monitor activity includes monitoring activity of an individual including detecting a sensor activated by an individual during the individual's daily activities. The embodiment also includes comparing the sensor activation to a predetermined sensor activation timeframe, determining whether to initiate an alert based upon the comparison, and checking for at least one other sensor activation to confirm whether an alert should be initiated.

34 Claims, 7 Drawing Sheets

(56) References Cited

U.S. PATENT DOCUMENTS

| | | | |
|---|---|---|---|
| 5,724,987 A | 3/1998 | Gevins et al. | |
| 5,810,747 A | 9/1998 | Brudny et al. | |
| 5,890,905 A | 4/1999 | Bergman | |
| 5,905,436 A * | 5/1999 | Dwight et al. | 340/573.1 |
| 6,042,383 A | 3/2000 | Herron | |
| 6,108,685 A | 8/2000 | Kutzik et al. | |
| 6,281,790 B1 | 8/2001 | Kimmel et al. | |
| 6,402,520 B1 | 6/2002 | Freer | |
| 6,520,905 B1 | 2/2003 | Surve et al. | |
| 6,524,239 B1 | 2/2003 | Reed et al. | |
| 6,540,674 B2 | 4/2003 | Zadrozny et al. | |
| 6,542,076 B1 | 4/2003 | Joao | |
| 6,558,165 B1 | 5/2003 | Curry et al. | |
| 6,626,676 B2 | 9/2003 | Freer | |
| 6,821,258 B2 | 11/2004 | Reed et al. | |
| 6,950,017 B2 * | 9/2005 | Smith | 340/521 |
| 6,950,026 B2 | 9/2005 | Yamashita et al. | |
| RE39,909 E * | 11/2007 | Taylor, Jr. | 340/573.4 |
| 2002/0198473 A1 | 12/2002 | Kumar et al. | |
| 2003/0004652 A1 | 1/2003 | Brunner et al. | |
| 2003/0063585 A1 * | 4/2003 | Younis et al. | 370/331 |
| 2003/0096590 A1 | 5/2003 | Satoh | |
| 2003/0114763 A1 | 6/2003 | Reddy et al. | |
| 2003/0117279 A1 | 6/2003 | Ueno et al. | |
| 2003/0130590 A1 | 7/2003 | Bui et al. | |
| 2003/0185436 A1 | 10/2003 | Smith | |
| 2003/0189485 A1 | 10/2003 | Smith | |
| 2003/0216670 A1 | 11/2003 | Beggs | |
| 2003/0229471 A1 | 12/2003 | Guralnik et al. | |
| 2003/0236451 A1 | 12/2003 | El-Nokaly et al. | |
| 2004/0131998 A1 | 7/2004 | Marom et al. | |
| 2004/0191747 A1 | 9/2004 | Atsumori et al. | |
| 2004/0219498 A1 | 11/2004 | Davidson | |
| 2005/0024199 A1 | 2/2005 | Huey et al. | |
| 2005/0057357 A1 | 3/2005 | Helal et al. | |
| 2005/0065452 A1 | 3/2005 | Thompson | |
| 2005/0073391 A1 | 4/2005 | Mizobuchi | |
| 2005/0131736 A1 | 6/2005 | Nelson et al. | |
| 2005/0137465 A1 | 6/2005 | Cuddihy et al. | |
| 2005/0231356 A1 * | 10/2005 | Bish et al. | 340/539.1 |
| 2005/0234310 A1 | 10/2005 | Alwan et al. | |
| 2005/0244797 A9 | 11/2005 | Klingberg | |
| 2005/0264425 A1 | 12/2005 | Sato et al. | |
| 2006/0055543 A1 * | 3/2006 | Ganesh et al. | 340/573.1 |
| 2006/0089538 A1 * | 4/2006 | Cuddihy et al. | 600/300 |
| 2006/0161218 A1 | 7/2006 | Danilov | |
| 2007/0032738 A1 | 2/2007 | Flaherty et al. | |
| 2007/0085690 A1 * | 4/2007 | Tran | 340/573.1 |
| 2007/0132597 A1 | 6/2007 | Rodgers | |
| 2007/0152837 A1 | 7/2007 | Bischoff et al. | |

FOREIGN PATENT DOCUMENTS

| | | |
|---|---|---|
| EP | 1 585 018 | 10/2005 |
| EP | 1585077 | 10/2005 |

OTHER PUBLICATIONS

Siddharth Dalal, et al., "A rule-based approach to the analysis of elders'activity data: Detection of health and possible emergency conditions", AAAI Fall Symp.—Tech Rep.

B. Majeed, et al., "Intelligent Systems for wellbeing monitoring", Intelligent Systems, 2004. Proceeding, Jun. 22, 2004, pp. 164-168, vol. 1.

* cited by examiner

MONITORING ACTIVITY OF AN INDIVIDUAL

CROSS REFERENCE TO RELATED APPLICATION

This application is a continuation of U.S. application Ser. No. 11/788,178, filed Apr. 19, 2007, which is a continuation in part of U.S. application Ser. No. 11/323,077, filed Dec. 30, 2005 now U.S. Pat. No. 7,589,637 issued Sep. 15, 2009, the entire specification of which in incorporated herein by reference.

BACKGROUND OF THE INVENTION

In the field of remote health monitoring, systems have been developed to enable an individual to contact medical professionals from their dwelling regarding a medical emergency. For example, in various systems, an individual is equipped with an emergency call button that initiates a call or signal to an emergency call center.

The concept of such a system is that if an individual has a health related problem, they can press the emergency call button and emergency medical providers will respond to assist them. However, in some cases, the individual is unable to press the emergency call button, such as when an individual has fallen and cannot reach the button, is rendered unconscious, or is cognitively impaired.

More complex systems have also been designed to monitor medication compliance or check health characteristics of an individual, such as heart rate, body temperature, blood chemistry, blood pressure, respiration, and the like. In these systems, the individual typically has to provide data periodically, such as by telephoning a monitoring center to provide health information to the center or by checking onto a web site or other data collection system.

For example, blood chemistry monitoring systems have been devised where an individual takes a sample of their blood, performs tests on the blood, and provides the results to medical professionals via a telephone line. The blood chemistry information is then reviewed by a medical professional in order to monitor the health of the individual. Neither of the above systems has the capability to detect if someone has become incapacitated and requires assistance.

Additionally, systems have been developed that use sensors within the home to monitor an individual within a dwelling. Typically, these systems include motion sensors, for example, that are connected to a base control system that monitors areas within the dwelling for movement. When a lack of movement is indicated, the system indicates the lack of movement to a remote assistance center that can contact a party to aid the individual. However, not all inactivity indicates that an individual is in need of assistance. For example, an individual can be sitting in a chair for a prolonged period, or lying in bed. These periods may be sufficient to initiate an alert for third party response, but may not actually be an emergency. In some of these systems, the system is designed to allow a third party to intervene to aid the individual according to the analysis of the information received by the remote assistance center.

Some systems also are designed such that the individual being monitored has to actively turn the system on and off (activate/deactivate) when leaving and returning to the dwelling to indicate whether the individual is home or away. This added step can be forgotten in some instances and thereby can cause the system to be ineffective at times.

Further, systems that use a number of sensors to monitor an individual and do analysis on the information collected typically use these sensors in isolation. Further, such systems also monitor the health of the system, and its sensors, based upon the individual sensor activations. That is, a sensor can be activated, but may not be correlated with any other sensors in the system. Accordingly, the certainties of the sensor activations of these systems and/or the determinations of whether to take an action by a system are based upon the reliability and reception of signals from individual sensors.

DETAILED DESCRIPTION OF THE INVENTION

Figure 1:
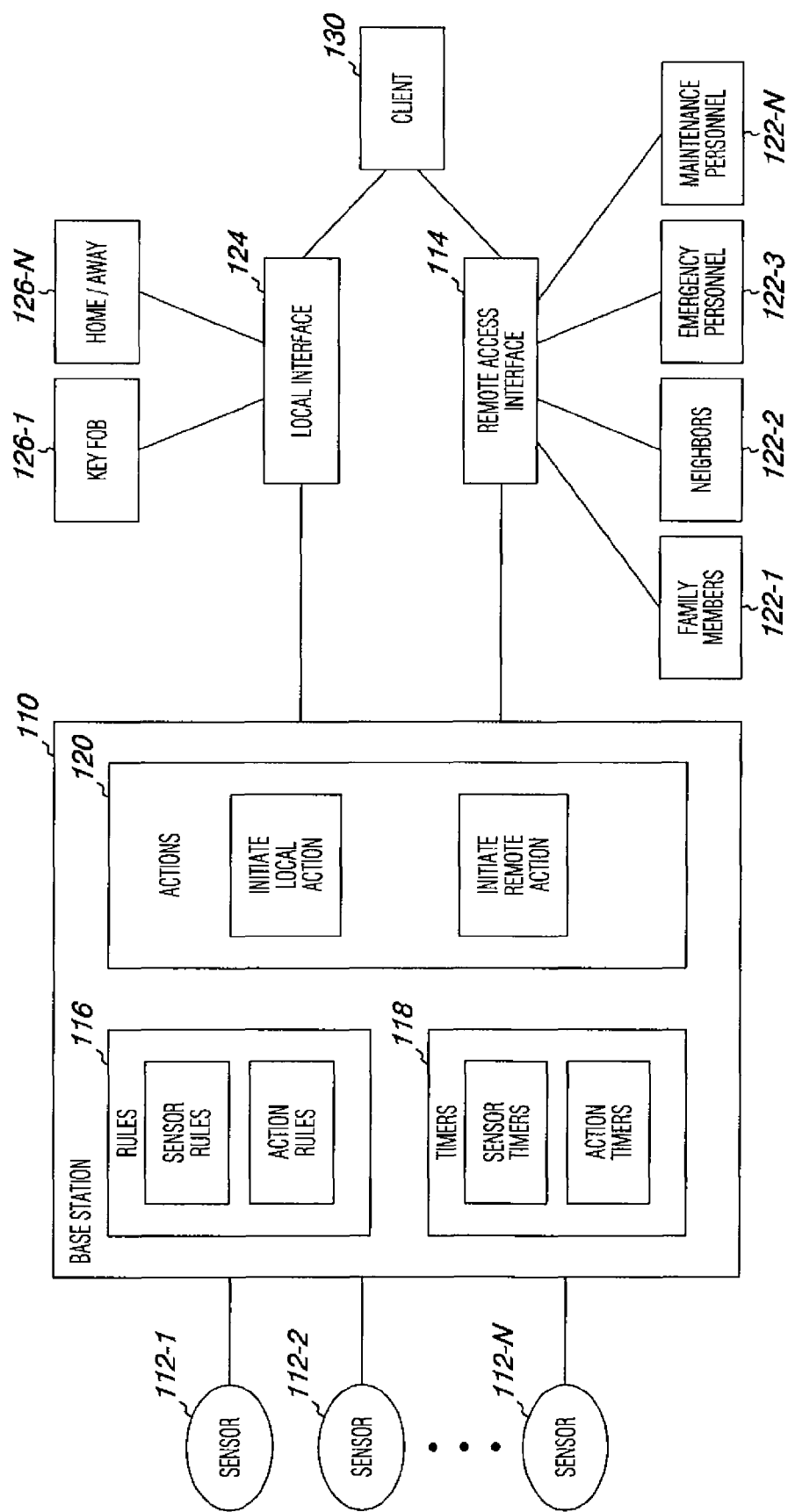
FIG. 1 illustrates a monitoring system embodiment.

Embodiments of the present invention can provide simple, cost effective, privacy-respecting, and relatively non-intrusive methods, devices, and systems for monitoring activity. Embodiments include systems to monitor the activity of an individual within a dwelling, such as a house, condominium, townhouse, apartment, or institution (e.g., hospital, assisted living facility, nursing home, prison, etc.)

Embodiments can provide automated detection of changes in activity within a dwelling and initiation of alerts to third parties to check on and/or assist the individual where assistance is needed, thereby avoiding prolonged periods of time before assistance is provided. Embodiments also can utilize multiple sensors, multiple timers, and multiple rules to determine whether to initiate an action, thereby increasing certainty that an action is necessary and should be initiated. Embodiments also can utilize multiple sensors, multiple timers, and multiple rules to make statistical correlations between a number of sensors, thereby increasing certainty that the system is in satisfactory health.

Embodiments can include a number of sensors that are connected to a variety of items within the dwelling to indicate the activity of the individual. For example, sensors can be connected to the client's bed to indicate that a client is lying on the bed. Sensors can also be used on drawers and cupboards to indicate when the individual opens a drawer or the door to a cupboard.

Many other types and uses for the sensors are described in more detail below. Various embodiments are designed to be transparent to the occupant of the dwelling and, therefore, such a system can monitor the daily routine of the occupant without the occupant having to interact with the system, such as by pressing buttons, logging onto websites, entering health data, and the like.

In various embodiments, a monitoring device and/or system can monitor the activity of an individual, for example, by detecting a sensor activated by an individual during the individual's daily activities. Systems and/or devices can also compare the pattern and/or frequency of sensor activations to a predetermined sensor activation timeframe, pattern, and/or frequency and determine whether to initiate an action based upon the one or more comparisons. In some embodiments, a number of sensors can be used to cross-check an indication that assistance may be needed or to determine whether an action should be taken or a timer should be reset.

For example, in some embodiments, a home/away sensor can be worn or carried by an individual (e.g. as a pendant). The sensor can indicate whether the individual is within a certain distance of the base station of the system, for instance, through use of a sensor. In various embodiments, a presence of an indication from a home/away sensor can be taken to mean that the home/away sensor is within range and that the individual possessing the home/away sensor is present in a monitoring area (e.g. in a "home" state). Similarly, in various embodiments, an absence of an indication from a home/away sensor can be taken to mean that the home/away sensor is out of range and that the individual possessing the home/away sensor is not present in a monitoring area (e.g. in an "away" state).

However, if the sensor is not working for some reason (e.g., the individual fell and it broke during the fall), it may indicate that the individual is away from the dwelling even though they are still at within a predetermined distance to the base station. In such instances, a logic component of the system can use other sensors to cross-check whether the home/away sensor activation is correct.

For example, the exit door sensors of the dwelling can be checked to see if the individual activated them, indicating that the individual did leave the dwelling. If no exit sensors were activated, then there is a likelihood that the individual is still within the dwelling.

The above example uses the home/away sensor as a trigger for initiating an action. In some embodiments, the system includes a set of rules for determining with more certainty whether the individual is really home or away. The system can include rules based software, firmware, or hardware to make this determination.

In this instance, the rules based logic component can initiate a timer which establishes a time period for making the determination. The system can then monitor the other sensors (e.g., the exit sensors) to detect any sensor activations and/or can review past sensor activations to identify if an exit door sensor was activated within a predetermined period preceding the activation of the home/away sensor. For such review, the system can include memory to store such information. In various embodiments, the system can also transmit such stored information to a remote server for analysis of the system's performance.

In such embodiments, the system can use individual sensors or groups of sensors for increasing the certainty that the first sensor is correct. For instance, categories include types of sensors (e.g., motion, water monitoring, contact, etc.), location within the dwelling (e.g., hallway, kitchen, bathroom, bedroom, etc.), or by daily activity (e.g., eating, transfer, waking, etc.). These groups can then be utilized to reduce the number of false positives that may be indicated by the system through use of a number of cross-checking algorithms (e.g., rules) to confirm that a situation where the user may need assistance is indicated. Various embodiments of the present disclosure can include one or more groups of sensors, grouped in various ways. These groups of sensors can also be added to, modified in, or deleted from the system.

The rules can then use such groups to make more specialized determinations. For example, the rules can define that an action should be taken if three sensors of the group have been activated. The rules can also provide that an action should be taken if a sensor in each group has been activated. In such embodiments, the events that confirm an initial indication of a need for assistance may also include separate timers, time periods, criteria, and/or protocols for confirming the initial indication. In various embodiments, each group can be associated with one or more timers and one or more rules.

This information can also be used to determine whether a sensor is malfunctioning. For example, if a sensor is positioned to monitor movement in a living room, however, its positioning is such that a car driving by activates the sensor, in some embodiments, the logic component can look at other sensors to see if other activations also indicate such movement (e.g., a chair sensor in the living room, a light switch sensor, or other such sensors). If the other sensors do not indicate the presence of the individual in the room, then the timer can be reset and, in some embodiments, an alert can be generated informing the client and/or a third party that the sensor should be adjusted. In such instances, the number of activations over a period could be used to diagnose whether the system should be adjusted.

The system, in some embodiments can allow for the recording of diagnostic information about a number of monitoring components. This information can also be compared with predetermined diagnostic information, in some embodiments. One or more alerts can thereby be initiated based upon the comparison.

With respect to the sensors, the diagnostic information such as the operational health of the sensor can be monitored in various manners. For example, each of the number of sensors can be designed to send a periodic signal indicating that the sensor is operational. The base station can also be designed to send out a signal to check the sensors.

FIG. 1 illustrates a monitoring system embodiment. The system utilizes the base station 110 to monitor the activities of a client (e.g., an individual) in and/or around a dwelling through use of a number of sensors 112-1, 112-2, and 112-N. The base station 110 can also initiate a number of actions based upon a number of rules implemented by the base station. These rules use the information obtained from the number of sensors to determine whether to initiate an action or not.

A base station device 110 includes a number of components providing a number of functions, as will be discussed in more detail below. In the embodiment of FIG. 1, the base station device 110 is illustrated with respect to its various functionalities. For example, the base station 110 is capable of using rules 116, and/or timers 118 to determine whether to initiate an action 120.

A logic component can be used to control the functions of the base station device 110. For example, the logic component can include executable instructions for providing such functions as handling received information from the sensors in the system, time-stamping received information such as sensor activation or system health functionality, among others. A logic component can include RAM and/or ROM, a clock, an input/output, and a processor, in some embodiments.

In various embodiments, a logic component can be designed such that a first condition is to be met before beginning to monitor a second condition. For example, a first sensor activation is detected and then a timer is started to monitor the time elapsed until another sensor activation from the same sensor, or in some embodiments, from a different sensor. For instance, the first condition can be represented by receiving a first signal from a first sensor and the second condition can be represented by waiting for a second signal from at least one of the number of sensors of the system.

The base station device can utilize the remote assistance center device to contact third parties that may be able to aid the client. The base station and the remote assistance center devices can each be any type of computing device capable of managing the functionality of receiving alert requests and initiating such requests. For example, suitable devices include personal computers, mainframe computers, network servers, and other such devices.

The base station device 110, as discussed in more detail below, includes program instructions to receive signals from the sensors 112-1 through 112-N that are generated by activation of a sensor. In various embodiments, signals can be generated in a binary (e.g., on/off) fashion, such that the sensor generates a signal when the object being sensed changes state. For example, with respect to a sensor on a door, one type of sensor that can be provided can operate such that when the door is closed, no signal is generated, but when the door is opened, a signal is generated.

Similarly, when the door is closed again, another signal may be generated. Since the signals can be either on/off, the signals are typically easy to track and the sensors are inexpensive. However, embodiments of the invention are not limited to the use of on/off type sensors and can include various types of sensing devices, including ones whose signal strengths scale to the size of the activation parameter, such as temperature, weight, or touch.

The sensors can be of various types, for example, types of sensors include: sensors to indicate the opening and closing of a door or drawer; sensors to indicate the movement of objects such as shades or blinds; current and/or voltage sensors to monitor appliances, lights, wells, etc.; pressure or fluid flow sensors to indicate the turning on and off of water; temperature sensors to indicate that the furnace is on or off; force sensors such as strain gauge sensors to sense an individual walking over a pad, sitting in a chair, or lying in bed; motion sensors to sense the motion of objects within the dwelling; and alert switches/buttons to signal an emergency or client input such as a cancellation request.

In some embodiments, a portable device having a sensor can be carried or worn by the client and can include a button or switch, for example, that can be used to cancel the alert. A client or other individual can also confirm that the alert has been received through use of a button or switch. Portable devices can be any type of device that is portable and that can provide the described functionalities. Examples can include basic devices, that have a sensor and the capability to provide power to the sensor, up to complex devices, having multiple functions. Examples of complex portable devices can include mobile phones and portable computing devices, such as PDA's and the like.

In various embodiments an alert can be canceled, for example, through use of an alert cancellation sensor activated either by an individual being monitored or by another individual activating the sensor. The sensor can be one of various sensors within the system and can be a button on the base station which senses when someone actuates the button.

The sensors can be analog and/or digital type sensors and can include logic circuitry and/or program instructions to transmit Boolean logic output to the base station device 110.

With regard to the system embodiment shown in FIG. 1, the system also includes a remote assistance center device (indicated as Remote Access Interface) 114 and a local interface 124, which are accessible by a client 130. The communication between the devices 110, 112-1 through 112-N, 114, and 124 can be accomplished in various manners. For example, in the embodiment shown in FIG. 1, the communications can be accomplished by wired (e.g., telephone line) and wireless (e.g., radio interface) communications. Further, the functionality of these devices can be provided in fewer devices than shown, or in more devices than shown.

In the embodiment of FIG. 1, system devices 126-1 through 126-N (where "N" represents a scalable number) can communicate with the base station 110, through the local interface 124. The system device can include a key fob 126-1 and a home/away sensor 126-N. The key fob 126-1 can, in some embodiments, provide access to and control of at least some of the functions of the base station 110 described herein.

The home/away sensor 126-N can, in various embodiments, be a portable device such as a wearable pendant, as described above. In various embodiments of the present disclosure, the home/away sensor 126-N can include communications using any of various communication protocols (e.g. IEEE 802.15.4, IEEE 802.11, and cellular protocols, to name a few). In such embodiments, an individual can wear the pendant while moving around inside their dwelling or outside near their dwelling while maintaining communication between the home/away sensor 126-N and the base station 110. The home/away sensor can also be provided in a key fob or other carried portable device.

In various embodiments, the system can include a portable device that utilizes a short range communication signal and/or a long range communication signal to communicate to a base station of the system. These communication types can be used in embodiments in a variety of ways. A number of these ways are described below.

In some embodiments, the home/away sensor can be used to indicate that the client is home based upon the home/away sensor's distance from the base station. For example, if a short range communication type is used, when the home/away sensor is out of range of the base station, the system can determine that the client is away. Short range communication types can include IEEE 802.15.4 and/or IEEE 802.11 protocols, for example. As discussed herein the certainty of such determinations can be increased by other sensor activations.

In various embodiments, the determination of whether the client is home or away can be accomplished, for example, by identifying the location of the home/away sensor. In such embodiments, the home/away sensor can be communicating via a long range communication type and the sensor can be located in various manners including via tracking of the communication signal, such as cellular triangulation, or other such mechanisms.

Some embodiments, can also use a long range communication type for the emergency call functionality. Such embodiments can include a portable device having an emergency call sensor (e.g., button) and/or a home/away sensor.

In this way, the emergency call function could be used while the client is at the store or down the street from their dwelling and, if used with a system having a short range home/away sensor, the system could also be indicating that the client is away. Further, through use of a longer range communication type, it may also be possible to locate the client based upon the communication signal as described above.

In various embodiments having a short range communication type for providing some of its functionality, the portable device may have the ability to communicate to another device having a long range communication capability. For example, in some embodiments, the portable device can include a short range emergency functionality. However, this portable device may be designed to interact with another device, such as a mobile phone or a computing device to communicate information to the base station of the system or to a third party.

As stated above, in some embodiments, an alert can be initiated by contacting a third party via a remote device. This can include contacting a remote assistance center device that can be used to make contact with a third party. For example, remote assistance centers can have a number of individuals accessing the remote assistance center device to review and/or respond to alert messages received by the remote assistance center device. These individuals can provide the assistance, and/or contact other third parties, such as neighbors, family members, emergency medical personnel, and/or other individuals that may be able to provide assistance. In some embodiments, the remote assistance center can have one or more of these functions automated by a computing device.

The remote assistance center device can include a list of third party contacts. These contacts can be compiled from the assistance center, from the client of the system, or from both sources, among others.

For example, a remote assistance center can have a number of individuals monitoring a number of remote assistance center devices. When a request to initiate an alert is received, the individual monitoring the remote assistance center device 114 can respond, the individual can contact another third party to respond, and/or the remote assistance center device 114 can contact a third party to respond, for instance.

As used in this disclosure, other individuals can include various third parties that may be summoned by the system to respond as discussed above.

In various embodiments, the individual receiving the alert can provide a confirmation that the individual is the party intended to receive the alert. This can be a voluntary submission or can be asked for by the remote assistance center.

These functions can be accomplished with audio, keypress, or other type of response either directly to the base station or by telephone. The remote assistance center can use a number of methods to decide which of the third parties to contact. For example, the selection of a third party can be based on the level of severity of the alert or the contacting hierarchy stipulated by the client.

In some embodiments, the base station can also include a display for displaying text, images, sound, and/or video thereon. Embodiments can also include a number of client interface components, such as buttons, switches, and the like, to allow a client to interact with the base station using the interface components on the device.

As stated above, in some embodiments, a number of sensors can be used to cross-check an indication that assistance may be needed. This can be accomplished, for example, by logic circuitry associated with the base station 110. The concept of cross-checking will be discussed in more detail below.

Figure 2:
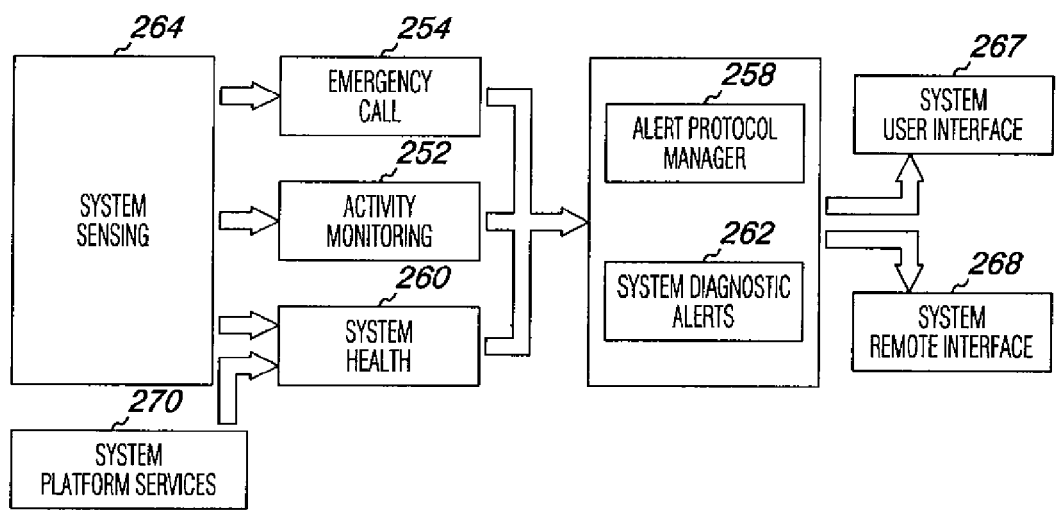
FIG. 2 illustrates an embodiment of base station data flow.

FIG. 2 illustrates an embodiment of base station data flow. This diagram illustrates the flow of information from various parts of the system. In the embodiment shown in FIG. 2, the system sensing information 264 can be used in a variety of functions provided by the system.

For example, system sensing information can be used to support emergency call functions 254, activity monitoring functions 252, and system health functions 260. Each of these latter functions (i.e., 252, 254, and 260) utilizes information about either a sensor or an activity of an individual that activates a sensor.

The blocks 252, 254, and/or 260 can process and interpret information from system sensing block 264 in order to provide information to the alert protocol manager functionality 258, and a system diagnostic alert protocol functionality 262. These functionalities can be provided at the base station and/or at a remote location, for example. Individually, blocks 252, 254, or 260 can pass system information directly to the alert protocol manager 258, or can process the information itself to determine the need to initiate an alert request or other action request to the alert protocol manager 258.

The alert protocol manager 258 can initiate an alert upon a request from 252, 254, or 260, or can further process the information received from 252, 254, or 260 to determine whether to initiate an alert or other action.

In the embodiment illustrated in FIG. 2, the initiation of an alert by the alert protocol manager 258 can be implemented through use of functions within the system client interface 267 and/or the system remote interface 268. In various embodiments, the system remote interface 268 can be a call center computer, such as a computer at an emergency call center. For example, an alert process can include a notification of the client that an alert will be or has been initiated. This can be brought to the client's attention to allow the client to cancel the alert if the need for an intervention does not exist or has passed. In such cases, the system client interface can be used to indicate the impending or existing alert condition and/or can be used by the client to confirm and/or cancel the alert.

The system remote interface can be used to contact a third party, such as a remote assistance center device to inform the third party that an alert condition exists and that aid may be needed. Aid can be a call to the client of the system, a visit by a third party (e.g., doctor, emergency medical personal, system technician, etc.) to the location of the client, or other such aid.

Similarly, system information can be provided from the system platform services block 270 to the system health block 260. This information can be used to determine whether to issue an alert for a fault in the system, for a software/firmware update, or the like. The system diagnostic alert block 262 can be used to issue such an alert. This alert can then be effectuated through the system client interface 267 and/or the system remote interface 268.

For example, if a sensor has to have a battery changed, the alert can be sent to both the client and a third party (e.g., via blocks 267 and 268). If the client changes the battery, the alert can be canceled and notification of the cancellation can be provided to the third party.

FIGS. 3A through 6B illustrate various method embodiments for monitoring activity. Unless explicitly stated, the method embodiments described herein are not constrained to a particular order or sequence. Additionally, some of the described method embodiments and elements thereof can occur or be performed at the same point in time. Method embodiments can be performed by computer executable instructions on software and/or firmware.

Figure 3A:
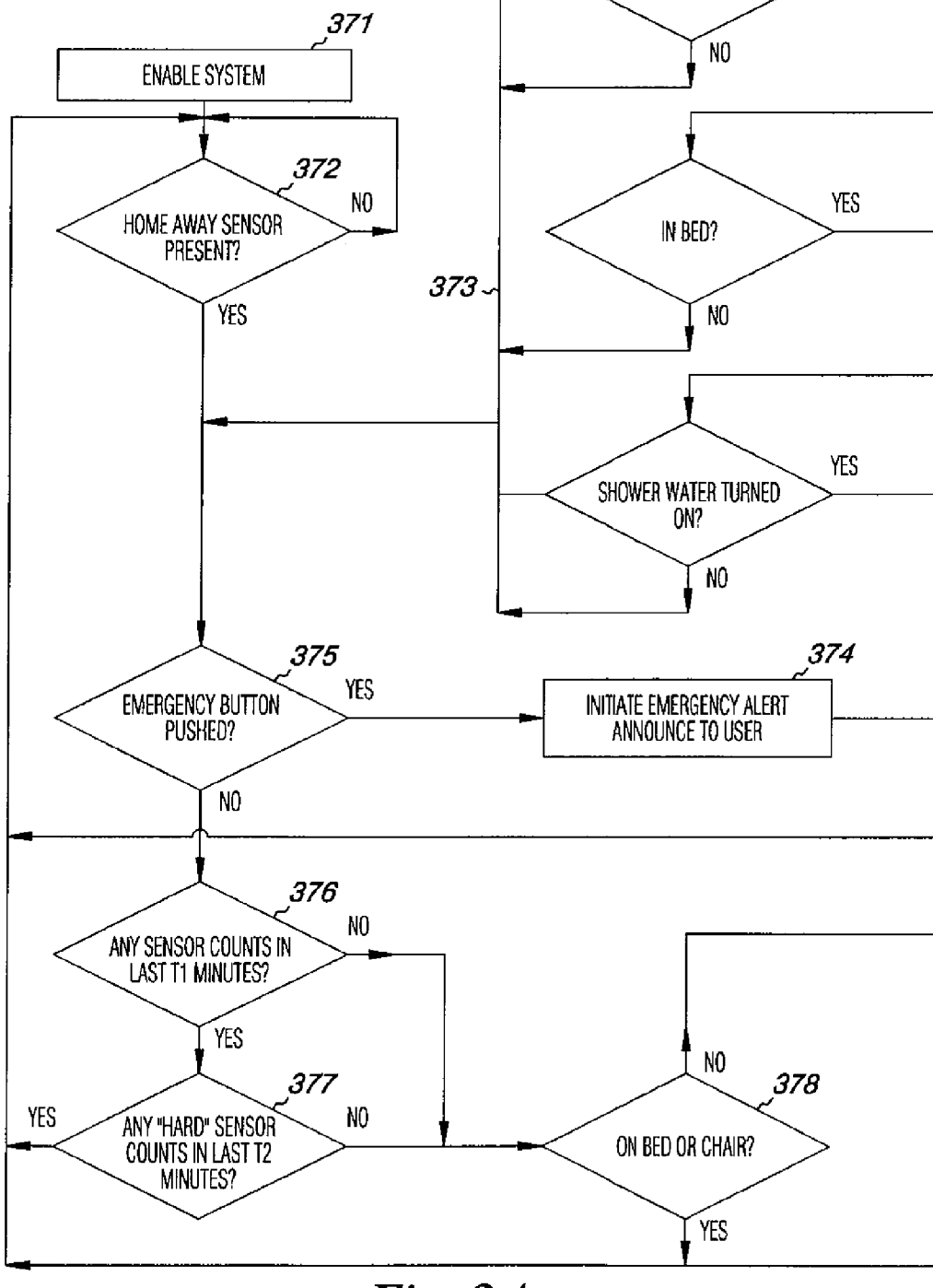
FIGS. 3A and 3B illustrate an embodiment of activity monitoring alert protocol management.
Figure 3B:
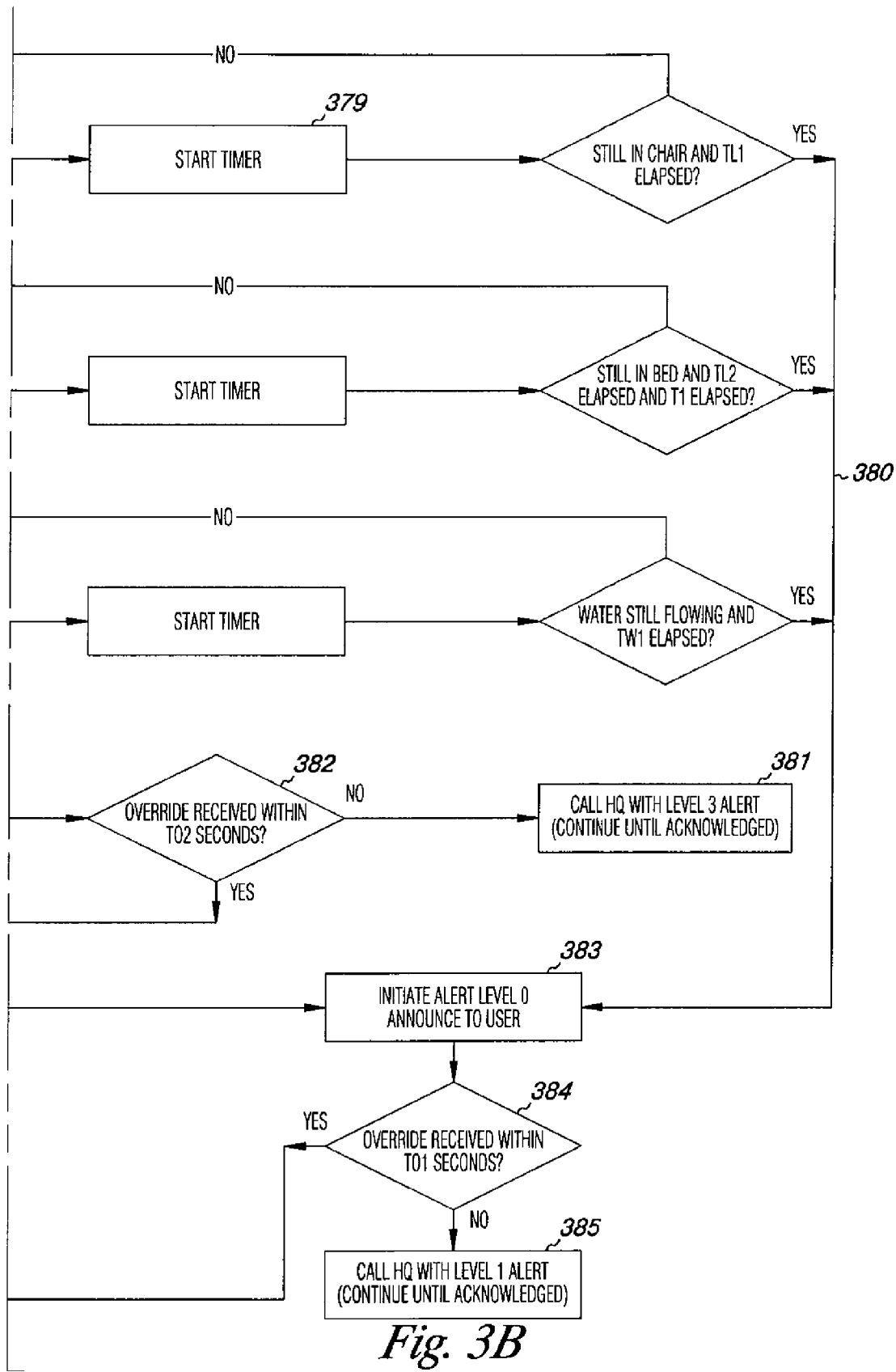

FIGS. 3A and 3B illustrate an embodiment of activity monitoring alert protocol management. The system can include other rule based protocol management operations similar in nature to the one provided herein as an example of such rule based protocols. Further, although five sensor types are illustrated in this example, various embodiments can include more or less sensors and sensor types and may or may not include the sensor types shown in the illustrated example.

The embodiment of FIGS. 3A and 3B can be accomplished by a number of executable instructions and/or through use of logic circuitry. In the embodiment illustrated in FIGS. 3A and 3B, the system is enabled at block 371. In such rule based systems, each possible result includes an action, such as to wait for another condition to be met or to perform an action, etc.

The home/away sensor can be used to indicate that an individual to be monitored is present or not within the monitoring area. In this way, if the individual is not present then false alert initiation based upon the absence of sensor activations during a prolonged period can be suppressed, among other benefits.

In the embodiment illustrated in FIGS. 3A and 3B, the home/away sensor is checked to identify if it is present at block 372. If it is not, then the system can cycle and recheck to see if the sensor is present at that later time. In some embodiments, the system can report an error after the system has accomplished a number of such cycles and rechecks. Additional system checks, including sensor checks can be accomplished at this point in the process as well as at other points in the process.

If the home/away sensor is indicated as present, the system begins checking a number of sensors within the system. In the embodiment illustrated in FIGS. 3A and 3B, the system checks to see if an emergency call button has been pressed at block 375. If it has been pressed, an alert announcement can be initiated to the individual being monitored, at block 374. The announcement can be audio, visual, and/or physical in nature.

In some embodiments, the system can provide the individual with an opportunity to override the emergency alert, at block 382. If the override is received, the system returns to its normal monitoring cycle. If not, the remote assistance center can be contacted, at block 381. The attempts to contact can be continued indefinitely, or for a period of time, until the alert has been acknowledged.

If the emergency sensor has not been activated at block 375, the system can check a number of other sensors of the system to identify whether any sensor, a certain sensor, or certain sensors have been activated during a particular period of time (e.g., parameterized as T1 minutes in this embodiment), at block 376. If no sensors have been activated during that period, then the system checks to see if the individual is in bed or on a chair based upon bed and/or chair sensor activation information, at block 378. In various embodiments, certain sensors, such as a bed and/or chair sensor, can be used to determine normal periods of inactivity. The system can use these certain sensors to distinguish normal periods of inactivity from abnormal periods of inactivity. This distinction enables the system to avoid some false alarms that would otherwise occur from normal periods of inactivity.

If the individual is not in bed or on a chair, the system announces the initiation of an alert to the individual at block 383. If an override is not received at block 384, the remote assistance center is contacted at block, 385.

If a sensor has been activated within the time period at block 376, in some embodiments, the system can check to see whether any "hard" sensor activations have been sensed in a parameterized time period (e.g., illustrated in FIG. 3 as T2 minutes), at block 377. If so, the normal monitoring loop is continued. If not, the system can check to see whether the individual is in bed or on a chair, at block 378, and the process described above with respect to that block is followed.

"Hard" sensors, as illustrated in the embodiment of FIG. 3, can be described as a group of sensors that are likely correlated to human activity and unlikely to have been activated by other possible activities or occurrences at the location. Such hard sensors can be identified, for example, by the installers of the system, a system administrator, and/or the manufacturer of the system, among others. One such example of a defined hard sensor group can be non-motion sensors. These sensors are typically less likely to be triggered by non-client based activity. However, hard sensors can be defined in other manners as discussed above.

With regard to the embodiment of FIGS. 3A and 3B, the various sensors of the system can be checked at various times during the monitoring of the system. For example, in the embodiment illustrated in FIGS. 3A and 3B, the system includes a shower sensor, a bed sensor, and a chair sensor. These sensors can be periodically checked after the system checks whether the home/away sensor is present.

In each instance, the sensor can be checked for activation as indicated at 373. If the sensor has been activated, a timer (e.g., at block 379) can be started to monitor the length of time since sensor activation (e.g., TL1, TL2 or TW1 depending upon the specific location being monitored by the particular sensor). In the embodiment illustrated, the system checks to identify whether the individual is still in the chair, the bed, or in the shower after a predetermined period. If not, the timer for the particular sensor can be reset to 0 minutes waiting for a later activation. If so, the timer will continue running and the cycle of checking sensor activation can be continued. If the individual is still in the bed, chair, or shower at the predetermined time for that sensor, in this embodiment, an alert can be initiated, at 380 and announced to the client, at block 383.

In some embodiments, the timer control can accommodate a short deactivation period followed by reactivation. For instance, if the client gets out of bed in the middle of the night to go to the bathroom, if the client returns to bed within the predetermined allowable deactivation period, and if another sensor in the location is activated during the period of absence, then the bed timer will continue running without interruption.

Other combinations of behavior can be accommodated. In such a case, the individual may have stepped out of the shower without turning off the shower and has done something else, such as answered the phone. In such instances, if a phone sensor is being used in the system, the activation of the phone sensor indicates that there may be a reason, other than a health issue, for the individual having the shower on for a prolonged period. In some embodiments, a wait time, as in the bed example above, can be used when multiple such sensors are activated. In some embodiments, the system can time out the shower timer and begin the phone timer since the system can assume that the individual is out of the shower and now on the telephone.

Further, if a sensor is malfunctioning or has become inoperable, a combination of sensors can be used to identify whether or not an alert should be initiated. For example, if the Home/Away sensor is not present, the system can check on or more other sensors to see if the other sensors confirm that the client is away from the base station.

This can be accomplished, for example, by looking at the exit door sensors to see if they have been activated. This provides some confirmation that the client is "away" from the dwelling.

In various embodiments, if the system determines that the client is "away," of claim 21, then the system can transmit an out-of-range message to an emergency button associated with the system. This out-of-range message can indicate to a client that the emergency button is not likely to work, since it is out-of-range.

As another example, an activation of a first sensor can be associated with a simultaneous activation of a second sensor. For instance, a sensor indicating the opening of a kitchen cupboard can be associated with a motion sensor in the kitchen.

In this instance, the system looks for the activation of the kitchen cupboard sensor and the kitchen motion sensor during a defined time period (e.g., nearly simultaneous, within a few seconds, etc.). If these sensors do not activate within the time period, then the system can identify the sensor that did not activate as possibly malfunctioning.

The time periods used by the system to determine whether to initiate an alert can be predetermined by the manufacturer of the system, the installer, and/or the client, in various embodiments. Additionally, the periods can be designed to be updated during the lifetime of the device.

In some embodiments, data can be retrieved from the system regarding the sensor activation patterns. This information can be used to provide technicians with data to adjust the periods for initiating alerts. Updating can also be accomplished by the client, and/or through use of algorithms that automatically adapt to the individual based upon analysis of the sensor activations, among other updating mechanisms.

This updating can be accomplished through use of a number of different mechanisms. For example, logic circuitry can be used to change (e.g., increment, decrement, or substitute) a timer value in order to keep the value within an acceptable range. The system can also be updated to change a rule. For example, a rule can be changed in order to change how the system checks system health, determines whether an action should be taken, or determines whether to reset a timer. Such time value and rule changes can be accomplished by hardware and/or executable instructions.

Locating and/or confirming the presence of a mobile sensor such as a wearable sensor within the monitored area can be accomplished in various manners, such as by initiating a ping signal from the transceiver to the wearable sensor. In such a case, the wearable sensor can also include a transceiver and can receive the ping signal and can respond. The transmission of the ping signal can be by any means, such as via a radio frequency, and the like.

In some embodiments, the sensor can be constructed to periodically check-in with the base station device, such as by sending a ping signal to the base station device via radio frequency or other such manner. In such embodiments, the sensor can be provided with energy saving executable instructions that allow the sensor to be in "sleep mode," where power usage is reduced, and then to "awaken" periodically to send a ping signal to the base station device. Once the signal is sent, the sensor can then return to "sleep mode." When in "sleep mode" the client can awaken the sensor manually, for instance, by pushing an emergency button.

If a response to the ping signal is received by the base station device, then the executable instructions can interpret that to mean that the individual is within the signal range of the base station device. If a deviation in a behavior routine has been identified and a ping response has been received, executable instructions can initiate an alert to the individual as has been discussed above.

If no response is obtained from the individual, then the executable instructions can determine which third party to contact. Other sensors can be used in combination with, or instead of, a sensor worn by the individual to determine whether the individual is within the dwelling. Examples of other sensors include, motion sensors, sensors on the interior/exterior/garage doors, sensors on the individual's automobile, and the like.

In some embodiments, the system can include a number of alert levels. For example, in the embodiment of FIGS. 3A and 3B, the system includes four alert levels (levels 0, 1, and 3 are described). In the illustrated embodiment, a level 3 alert is the highest level and supercedes other alerts that may have been issued. A level 3 alert can also indicate to the remote assistance center that the individual is in urgent need of aid.

The level 0 alert is the alert initiated to the individual that can be overridden before another alert is issued. The alert issued if the level 0 alert is not overridden is a level 1 alert that can be used to indicate that the individual has not responded after a level 0 alert has be initiated. This can indicate to the remote assistance center that the individual may not be able to respond to the alert and therefore, aid should be provided.

The intervention at this level of alert can be by phone and/or in person, for example. It should be noted that although a level 2 alert is not shown in the diagram of FIGS. 3A and 3B, in some embodiments, the level 2 alert can be used to indicate that a component of the system may have to be repaired or replaced and that the individual being monitored and/or a technician should check the component. Such level 2 alert processes can be implemented in various manners similar to those described with respect to level 1 and 3 alerts.

Figure 4:
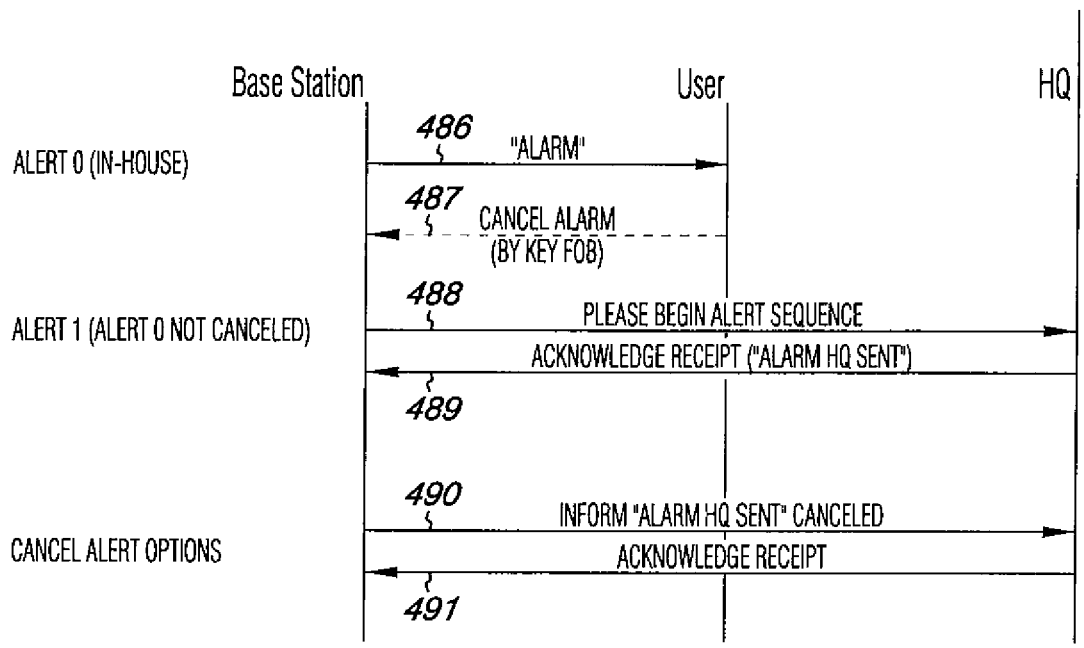
FIG. 4 illustrates an activity monitoring interaction process between a client and a remote device utilizing an embodiment of the present disclosure.
Figure 5:
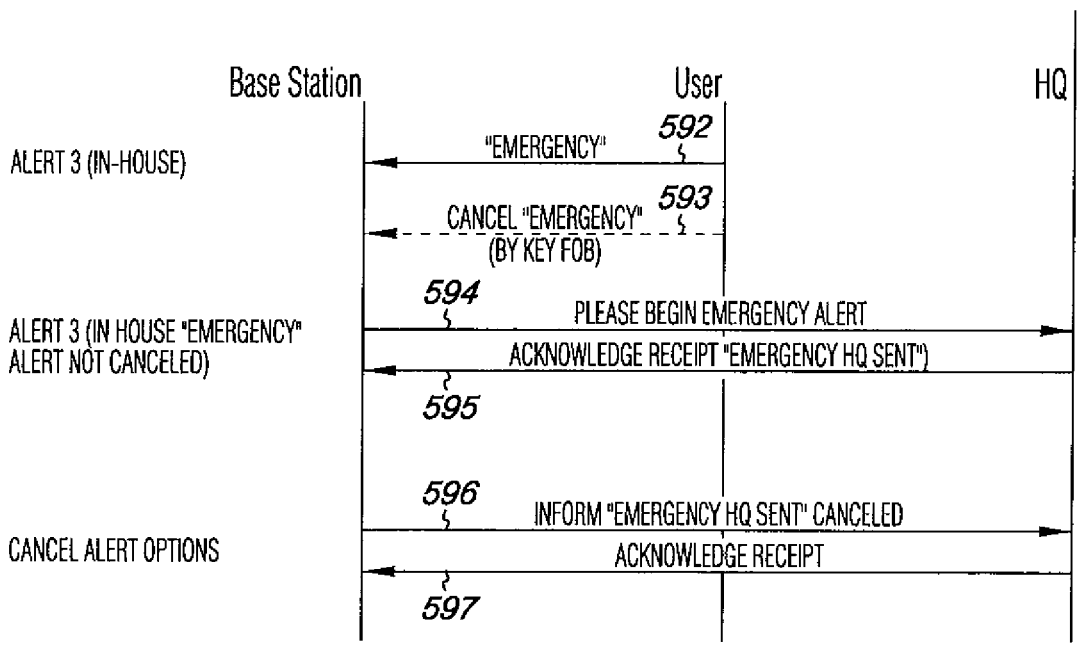
FIG. 5 illustrates an emergency alarm interaction process between a client and a remote device utilizing an embodiment of the present disclosure.

FIGS. 4 and 5 illustrate the initiation of alerts in an embodiment having various levels of alerts. FIG. 4 illustrates an activity monitoring interaction process between a client and a remote device utilizing an embodiment of the present disclosure. In the embodiment shown in FIG. 4, an alert is initiated by the system, in this example, by an alarm being activated at 486.

At this point the alert can be canceled, for example, by pressing a button on a key fob carried by the individual or a button on the base station device, among other cancellation mechanisms. If the alert is not canceled within a predetermined period, a level 1 alert is initiated. In initiating the alert, a message is provided to the remote assistance center at 488 to begin a predetermined alert sequence, such as to make a phone call to the individual being monitored, to send a third party to check on the individual, to send medical personnel, and the like.

In the embodiment shown, the system can continue to send this initiation message to the remote assistance center until an acknowledge receipt message is received at 489. This embodiment also includes the ability for the base station to provide a cancellation message, in order to cancel the alert sequence if the individual responds after the predetermined time to respond to the level 0 alert has expired at 490. The base station can continue to send this message until a confirmation of the cancellation message has been acknowledged as received by the remote assistance center at 491.

FIG. 5 illustrates an emergency alarm interaction process between a client and a remote device utilizing an embodiment of the present disclosure. Similarly, in the embodiment shown in FIG. 5, an emergency alert is initiated by the system at 592.

As with the embodiment of FIG. 4, the alert can be canceled at 593. If the alert is not canceled within the predetermined period, the level 3 alert is forwarded to the remote assistance center at 594 to begin a predetermined emergency alert sequence.

In the embodiment shown, the system can continue to send this initiation message to the remote assistance center until an acknowledge receipt message is received at 595. This embodiment also includes the ability for the base station to provide a cancellation message, in order to cancel the alert sequence if the individual responds after the predetermined time to respond to the alert has expired at 596. The base station can continue to send this message until a confirmation of the cancellation message has been acknowledged as received by the remote assistance center at 597.

Figure 6A:
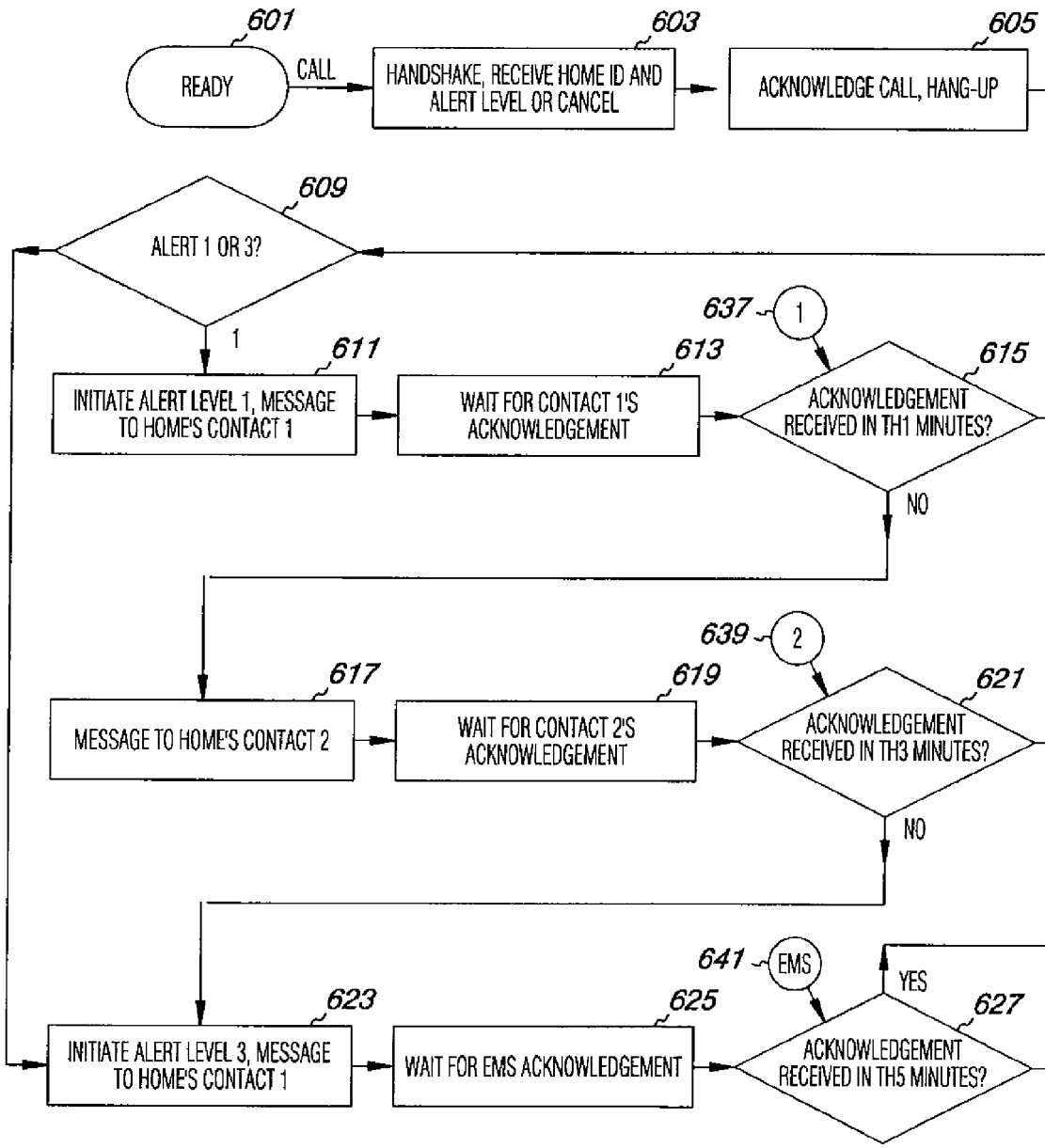
FIGS. 6A and 6B illustrate an embodiment of an interaction with a remote device regarding an alert condition.
Figure 6B:
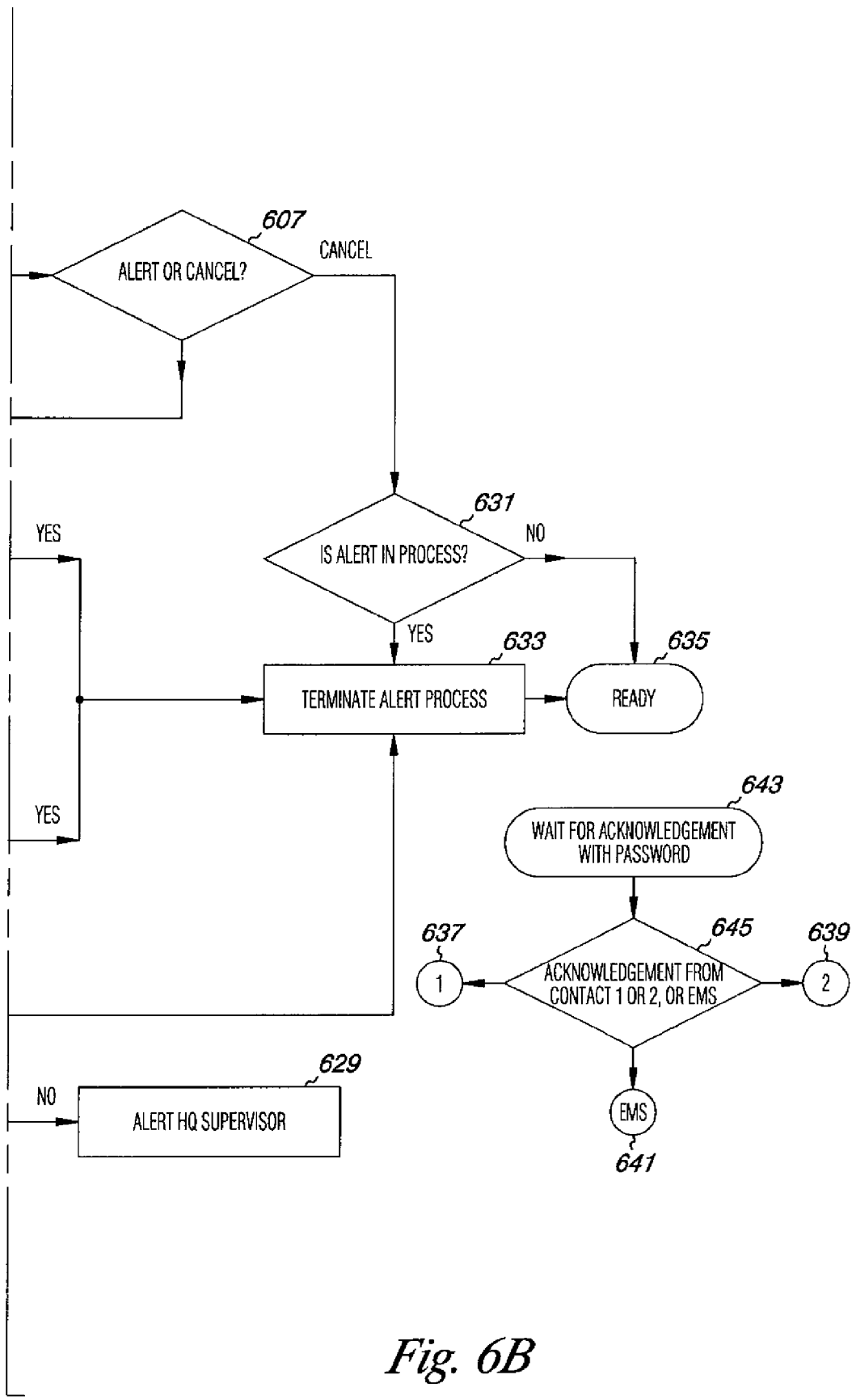

FIGS. 6A and 6B illustrate an embodiment of an interaction with a remote device regarding an alert condition. In this embodiment, the system begins to initiate contact with the remote assistance center, at 601, by making a connection with (e.g., placing a call to) the remote assistance center. In some embodiments, the first contact can be to the client as a message to cancel the alarm if intervention is not needed. In the embodiment illustrated in FIGS. 6A and 6B, the base station and remote assistance center exchange information at 603 (e.g., handshake, home/client ID, alert level/cancel).

The receipt of the information is acknowledged (e.g., an acknowledgement message can be sent to the base station) and disconnected at 605. Based upon the information provided, the remote assistance center determines whether the message is an alert request or a cancellation of an alert.

If the message is a request for an alert, then the type of alert is also determined. If the message was to cancel an alert, then the system is checked to determine if an alert is in process and, if so, the alert is canceled and the system returned to ready mode until another message is received.

In the embodiment illustrated in FIGS. 6A and 613, once the remote assistance center has identified the type of alert, it contacts one of a number of third parties. In the case shown, these parties have been determined based upon selections made by the individual being monitored, however, any third party contacts can be used and can be provided by parties such as, the manufacturer, the remote assistance center, another service provider, the individual's family members and the like.

The system initiates an alert to the first contact on the list of contacts for the particular individual being monitored at 611. In some embodiments, different third parties, or the order of the parties, can be different from one alert level to another. For example, the level 1 alert can have the individual, a first family member, a neighbor, and contact information for medical personal, while the level 3 alert can have the individual, medical personal, or a family member. The communications to different third parties can include identification information (e.g., name, telephone number, address) and/or medical information (e.g., diabetic or heart disease status, allergies to medicines, etc.).

In some embodiments, once an alert message is provided to a third party, the system can be designed to wait for an acknowledgement of receipt of the message from the third party at 613. If an acknowledgement is received at 615, then the alert process can be reset since a third party has received the message and presumably will aid the individual.

If no acknowledgement has been received after a predetermined period of time, the system can be designed to contact a second third party contact at 617. Again, in some embodiments, the system can wait for an acknowledgement to be received at 619, and, if received or not acknowledged at 621, the system can react to those conditions as described above. The system can continue to work down a third party contact list beyond the second contact if the system is desired to have such functionality. In some embodiments, a single contact can be provided.

In various embodiments, the above process can be accomplished entirely through logic on the base station and, therefore, a remote center device may not be necessary for contacting third parties. In such embodiments, the confirmations and communicating steps that are done between the two devices can be eliminated, since one device is providing the functionality.

In the embodiment illustrated in FIGS. 6A and 6B, if the second third party contact does not respond at 621, the system can then issue a level 3 alert and contact one of the third parties regarding the level 3 alert at 623. In this case, an emergency medical service (EMS) has been designated as the contact regarding level 3 alerts. In this case, the system is designed to wait for an acknowledgement from the EMS at 625.

In this embodiment, if the acknowledgement is not received at 627, contact is made to the remote assistance center supervisor so that another action can be devised at 629.

If the acknowledgement has been received, the alert process can be terminated at 633 and reset at 635 for the system to continue routine monitoring.

In some embodiments, the system can include a security process such that a third party responding can be identified as the correct party to respond to the alert. For example, in the embodiment of FIGS. 6A and 6B at 643, a password can be provided by the third party to ensure that they are the correct party.

In this way, other parties will not be able to respond erroneously or incorrectly to the alert message, thereby providing more certainty that the third party will render aid to the individual. In various embodiments, an acknowledgement, such as *11 can be used allow the third party to indicate that they have heard, understood, and acknowledged the message.

Once the password is provided, the third party can provide the acknowledgement at 645. Such a feature can be provided for first and second contacts as well as for the EMS and other contacts (as illustrated in the embodiment of FIGS. 6A and 6B at 637, 639, and 641, respectively).

The communication between the remote assistance center and the third parties can be provided in a number of formats, including but not limited to physical, visual, and audible messages. Examples of suitable formats include, voice messages, text messages, the illumination of lights such as those on the base station, and the like.

Although specific embodiments have been illustrated and described herein, those of ordinary skill in the art will appreciate that an arrangement calculated to achieve the same techniques can be substituted for the specific embodiments shown. As one of ordinary skill in the art will appreciate upon reading this disclosure, various embodiments of the invention can be performed in one or more devices, device types, and system environments including networked environments.

Combination of the above embodiments, and other embodiments not specifically described herein will be apparent to those of skill in the art upon reviewing the above description. The scope of the various embodiments of the invention includes other applications in which the above structures and methods can be used. Therefore, the scope of various embodiments of the invention should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method using computer-executable instructions stored on a non-transitory computer-readable medium executed by a processor for monitoring activity of an individual, comprising:

grouping a number of sensors into a first group associated with an activity of daily living of an individual and a number of sensors into a second group associated with the activity of daily living of the individual;

monitoring the number of sensors in the first group to identify activations of at least one sensor in the first group, wherein activations of at least one sensor in the first group indicate performance of the activity of daily living;

associating a number of rules defining a number of actions to be taken based upon activations of the at least one sensor in the first group; and applying a rule associated with the activation of the at least one sensor in the first group to determine whether to take an action, wherein the rule includes checking for at least one other sensor activation of at least one sensor in the second group to confirm whether the action should be initiated, wherein activation of at least one sensor in the second group indicates performance of the activity of daily living and activation of another sensor in the second group indicates that performance of the activity of daily living has ended.

2. The method of claim 1, wherein the method includes regrouping the number of the sensors into one or more different groups.

3. The method of claim 1, wherein the rule includes checking for a sensor activation from another sensor within the first group.

4. The method of claim 1, wherein the grouping a number of sensors into the first group and the second group is based upon one or more rules used to determine whether the action should be initiated.

5. The method of claim 1, wherein the method includes detecting a first sensor in the first group of sensors.

6. The method of claim 5, wherein checking for at least one other sensor activation includes checking for a sensor activation from a sensor within the second group of sensors that includes all sensors except the first group of sensors.

7. The method of claim 5, wherein checking for at least one other sensor activation includes checking for a sensor activation from a sensor within the second group of sensors that includes all sensors except the first sensor after detecting the first sensor in the first group.

8. The method of claim 1, wherein the method includes checking for at least one other sensor activation includes checking for a sensor activation from a third group defined by another daily living activity.

9. The method of claim 1, wherein monitoring the number of sensors in the first group to identify activations of at least one sensor in the first group includes detecting absence of a home/away sensor and wherein checking for at least one other sensor activation includes checking for a sensor activation from a sensor indicating an exit.

10. The method of claim 1, wherein the method includes utilizing a number of timers to determine whether to take the action.

11. The method of claim 1, wherein the method includes utilizing a number of timers to monitor whether a sensor activation occurs within a time period in order to determine whether to take the action.

12. The method of claim 1, wherein the method includes utilizing a number of timers to monitor whether a client response occurs within a time period in order to determine whether to take the action.

13. A system for monitoring activity, comprising:
a number of sensors to be activated by an individual;
a logic component having computer-executable instructions stored on a non-transitory computer-readable medium executed by a processor to:
institute multiple rules for determining whether to initiate an alert based upon one or more activations of the sensors;
initiate a first rule based upon an identification of a first sensor activation;
initiate a first timer for monitoring a sensor activation according to the first rule;
initiate a second timer for monitoring the time between a first sensor activation and at least one second sensor activation according to the first rule;
determine whether an action should be initiated based upon the analysis of whether the first rule has been met; and
modify a portion of the first rule which defines a time period to wait between the first sensor activation and the at least one second sensor activation based on the second timer monitoring the time between the first sensor activation and the at least one second sensor activation.

14. The system of claim 13, wherein the logic component is designed to initiate a second rule, associating a simultaneous activation of the first sensor and the second sensor.

15. The system of claim 13, wherein the logic component is designed to initiate the first rule based upon the identification of the first sensor activation wherein the first rule states that if the first sensor activation is detected, wait a predetermined time for a second sensor activation.

16. The system of claim 15, wherein the first rule further states, if a second sensor activation is not received then initiate an action.

17. The system of claim 15, wherein the first rule further states, if a second activation is received then reset the second timer.

18. The system of claim 13, wherein the first rule is modified to adjust the predetermined time to wait for the second activation based on the time between the first sensor activation and a third sensor activation.

19. The system of claim 13, wherein the first rule is modified to adjust the predetermined time to wait for the second activation based on the time between the first sensor activation and the at least one second sensor activation.

20. The system of claim 19, wherein the first sensor is a home/away sensor and wherein the logic component is designed to initiate the first rule based upon the identification of absence of the home/away sensor and check whether an associated sensor indicating an exit has been activated.

21. The system of claim 20, wherein if the home/away sensor is out of range to communicate with a base station, then an out-of-range message is displayed on a portable device.

22. The system of claim 13, wherein the first rule states if an emergency sensor is activated, then wait a predetermined period for receipt of a cancellation request, if no cancellation request is received, then initiate an action.

23. The system of claim 22, wherein the action is to initiate contact to a remote site.

24. A system for monitoring activity, comprising:
a number of sensors to be activated by an individual;
a logic component having computer-executable instructions stored on a non-transitory computer-readable medium executed by a processor to:
institute multiple rules for determining whether to initiate an action based upon one or more activations of the sensors;
initiate a first rule based upon an identification of a first sensor activation of the number of sensors;
initiate a timer for monitoring the time between the first sensor activation and at least one second sensor activation according to the first rule;

determine whether an action should be initiated based upon the analysis of whether the first rule has been met; and change a timer value for the time between the first sensor activation and the at least one second sensor activation that determines whether an action should be initiated based on the time between the first sensor activation and the at least one second sensor activation.

25. The system of claim 24, wherein the logic component is designed to initiate a timer for monitoring the time between the first sensor activation in a first group of sensors and at least one second sensor activation within the sensors of the first group.

26. The system of claim 24, wherein the logic component is designed to initiate a timer for monitoring the time between the first sensor activation in a first group of sensors and at least one second sensor activation from a sensor of a second group.

27. The system of claim 26, wherein the second group of sensors is defined as all sensors associated with the system after the first sensor activation in the first group of sensors.

28. The system of claim 26, wherein the second group of sensors is all sensors associated with the system except the sensor associated with the first sensor activation.

29. The system of claim 26, wherein the second group of sensors is all sensors associated with the system except the sensors associated with the group of sensors in which the first sensor activation was detected.

30. The system of claim 24, wherein the logic component changes the timer value in order to keep the value within an acceptable range.

31. The system of claim 24, wherein the logic component changes one or more of the multiple rules.

32. The system of claim 24, wherein the number of sensors includes a portable sensor that can be located based upon a communication signal.

33. The system of claim 24, wherein the system includes a portable device that utilizes a short range communication signal and a long range communication signal.

34. The system of claim 33, wherein the short range communication signal is provided by the portable device and the long range communication signal is accessed via another device.

* * * * *